(12) United States Patent
Okamura et al.

(10) Patent No.: US 10,245,411 B2
(45) Date of Patent: Apr. 2, 2019

(54) MEDICAL ELONGATED BODY

(71) Applicant: TERUMO KABUSHIKI KAISHA, Shibuya-ku, Tokyo (JP)

(72) Inventors: Ryo Okamura, Fujinomiya (JP); Kazuya Omata, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 15/921,734

(22) Filed: Mar. 15, 2018

(65) Prior Publication Data
US 2018/0200479 A1 Jul. 19, 2018

Related U.S. Application Data

(63) Continuation of application No. PCT/JP2016/078508, filed on Sep. 27, 2016.

(30) Foreign Application Priority Data

Sep. 29, 2015 (JP) .................................. 2015-191138

(51) Int. Cl.
*A61M 25/00* (2006.01)
*A61M 25/06* (2006.01)
(Continued)

(52) U.S. Cl.
CPC ........ *A61M 25/0045* (2013.01); *A61M 25/00* (2013.01); *A61M 25/06* (2013.01);
(Continued)

(58) Field of Classification Search
CPC .. A61M 25/0045; A61M 25/00; A61M 25/06; A61M 25/0662; A61M 2025/0046;
(Continued)

(56) References Cited

U.S. PATENT DOCUMENTS

| 4,100,309 A | 7/1978 | Micklus et al. |
| 5,229,211 A | 7/1993 | Murayama et al. |
| 6,893,427 B1 | 5/2005 | Jimenez |

FOREIGN PATENT DOCUMENTS

| JP | 59-19582 B2 | 5/1984 |
| JP | 7-83761 B2 | 5/1992 |

(Continued)

OTHER PUBLICATIONS

International Search Report (PCT/ISA/210) dated Jan. 17, 2017, by the Japanese Patent Office as the International Searching Authority for International Application No. PCT/JP2016/078508.
(Continued)

*Primary Examiner* — Michael C Miggins
(74) *Attorney, Agent, or Firm* — Buchanan Ingersoll & Rooney PC

(57) ABSTRACT

A medical elongated body including a tubular main body and a hub connected to the tubular main body. The medical elongated body includes a strain relief supported by a distal portion of the hub. The strain relief surrounds a predetermined range of the proximal portion of the tubular main body. The medical elongated body includes a hydrophilic lubricating coating layer and a temperature responsive lubricating coating layer on the outer surface of the tubular main body, the temperature responsive lubricating coating layer being proximal to the hydrophilic lubricating coating layer. The hydrophilic lubricating coating layer exhibits lubricating characteristics when wet. The temperature responsive lubricating coating layer exhibits hydrophilic characteristics and lubricating characteristics at a temperature lower than a critical temperature when wet and exhibits hydrophobic characteristics and non-lubricating characteristics at a temperature equal to or higher than the critical temperature when wet.

20 Claims, 4 Drawing Sheets

(51) Int. Cl.
  *C08L 27/06* (2006.01)
  *C08L 35/08* (2006.01)
  *A61L 29/10* (2006.01)
  *B05D 5/08* (2006.01)
  *C08L 75/04* (2006.01)
(52) U.S. Cl.
  CPC ......... *A61M 25/0662* (2013.01); *C08L 27/06* (2013.01); *C08L 35/08* (2013.01); *A61L 29/10* (2013.01); *A61M 2025/0046* (2013.01); *A61M 2025/0675* (2013.01); *B05D 5/08* (2013.01); *C08L 75/04* (2013.01)
(58) Field of Classification Search
  CPC ............ A61M 2025/0675; C08L 27/06; C08L 35/08; C08L 75/04; A61L 29/10; B05D 5/08
  See application file for complete search history.

(56) References Cited

FOREIGN PATENT DOCUMENTS

JP    2001-224695 A    8/2001
JP    2007-144062 A    6/2007

OTHER PUBLICATIONS

Examination Report No. 1 dated May 2, 2018, by the Australian Patent Office in Australian Patent Application No. 2016329461 (3 pages).
English Translation of the the Written Opinion (PCT/ISA/237) dated Jan. 17, 2017, by the Japan Patent Office as the ISA for International Application No. PCT/JP2016/078508.

MEDICAL ELONGATED BODY

CROSS-REFERENCES TO RELATED APPLICATIONS

This application is a continuation of International Application No. PCT/JP2016/078508 filed on Sep. 27, 2016, and claims priority to Japanese Application No. 2015-191138 filed on Sep. 29, 2015, the entire content of both of which is incorporated herein by reference.

TECHNICAL FIELD

The present invention generally relates to a medical elongated body used in a medical device.

BACKGROUND ART

In the medical field, various techniques using a medical device which includes a slender hollow tube may be performed. As an example, a technique for percutaneously introducing various types of catheter devices or the like into a living body is performed using an introducer configured to have an introducer sheath. The introducer sheath includes a sheath tube and a dilator which is assembled in the introducer sheath during use.

The introducer sheath is percutaneously introduced into a body cavity (for example, a blood vessel) of a living body from a distal side (i.e., distal end) of the sheath tube. A hollow portion formed inside the sheath tube is utilized as an access path connecting the inside and the outside of a living body in a state where the distal side of the sheath tube is introduced into the living body and a proximal side of the sheath tube is exposed by a predetermined length to the outside of the living body.

For example, there is a proposal in Japanese Patent Application No. 2007-144062 to provide a coating layer, which exhibits lubricating characteristics when wet, on an outer surface of a sheath tube. The coating layer helps the insertion and removal of the sheath tube with respect to a living body to be smooth and in a low-invasive manner.

SUMMARY OF THE INVENTION

When a coating layer such as that disclosed in Japanese Patent Application No. 2007-144062 is provided on an outer surface of a sheath tube, insertion characteristics with respect to the inside of a living body and movement characteristics at the time of pulling the sheath tube out of the living body become excellent (i.e., insertion, movement within the body, and removal of the sheath tube are relatively easier than when no coating layer is provided). On the other hand, there are cases where an imprudent movement (i.e., unintended or undesired movement) of the sheath tube is caused due to lubricating characteristics manifested by a part which is always in contact with a body fluid and the like inside a living body while a technique using an introducer sheath is performed.

The disclosure here involves a medical elongated body which can be smoothly put in (i.e., introduced and moved within) and taken out of a living body in a low-invasive manner and which can prevent an imprudent movement from occurring while being in use.

The disclosed medical elongated body includes a tubular main body that includes a hollow portion extending in an axial direction, a hub that is connected to the tubular main body on a proximal side, and a strain relief that is supported by the hub on a distal side and surrounds a predetermined range of the tubular main body on the proximal side. A hydrophilic lubricating coating layer which exhibits lubricating characteristics when wet, and a temperature responsive lubricating coating layer which exhibits hydrophilic characteristics and lubricating characteristics at a temperature lower than a critical temperature when wet and exhibits hydrophobic characteristics and non-lubricating characteristics at a temperature equal to or higher than the critical temperature when wet are formed on an outer surface of the tubular main body. The temperature responsive lubricating coating layer is disposed on the proximal side relative to the hydrophilic lubricating coating layer and is formed on the proximal side of the tubular main body.

In another aspect, the disclosed medical elongated body includes a tubular main body and a hub connected to the tubular main body. The medical elongated body includes a strain relief supported by a distal portion of the hub. The strain relief surrounds a predetermined range of the proximal portion of the tubular main body. The medical elongated body includes a hydrophilic lubricating coating layer and a temperature responsive lubricating coating layer on the outer surface of the tubular main body, the temperature responsive lubricating coating layer being proximal to the hydrophilic lubricating coating layer. The hydrophilic lubricating coating layer exhibits lubricating characteristics when wet. The temperature responsive lubricating coating layer exhibits hydrophilic characteristics and lubricating characteristics at a temperature lower than a critical temperature when wet and exhibits hydrophobic characteristics and non-lubricating characteristics at a temperature equal to or higher than the critical temperature when wet.

A medical elongated body is also disclosed that includes a tubular main body comprising a lumen extending in an axial direction, the tubular main body possessing an outer surface, the tubular main body comprising a first portion, a second portion and a third portion in the axial direction, the second portion being immediately adjacent and distal to the first portion, the third portion being immediately adjacent and distal to the second portion. The medical elongated body includes a hub connected to the first portion of the tubular main body. A temperature responsive lubricating coating layer which exhibits a first lubricity when being at a temperature lower than a critical temperature when wet and exhibits a second lubricity when being at a temperature equal to or higher than the critical temperature when wet is provided, the temperature responsive lubricating coating layer directly contacting the outer surface of the tubular main body along at least the second portion of the tubular main body. The medical elongated body includes a hydrophilic lubricating coating layer which possesses a third lubricity when wet, the hydrophilic lubricating coating layer directly contacting the outer surface of the third portion of the tubular main body. The second lubricity imparts greater frictional resistance than the first lubricity when the tubular main body moves within a living body, and the second lubricity imparts greater frictional resistance than the third lubricity when the tubular main body moves within the living body.

In yet another aspect, the disclosure here involves a method including: inserting an elongated tubular body into a living body, the elongated tubular body comprising an outer surface, the elongated tubular body comprising a first portion and a second portion being immediately adjacent and proximal to the first portion in an axial direction, the first portion of the elongated tubular body possessing a first frictional resistance, the second portion of the elongated tubular body possessing a second frictional resistance; heating the first portion and the second portion of the elongated tubular body due to the living body having a higher temperature than a surrounding environment, the first frictional resistance of the first portion of the elongated tubular body remaining constant throughout the heating of the first portion of the elongated tubular body, the second frictional resistance of the second portion of the elongated tubular body increasing in frictional resistance due to the heating of the second portion of the elongated tubular body; fixing the second portion of the elongated tubular body at a location of the living body by friction created between the second portion of the elongated tubular body and a location of the living body.

In the medical elongated body described above, it is possible to smoothly move the tubular main body in a low-invasive manner because each of the hydrophilic lubricating coating layer and the temperature responsive lubricating coating layer exhibits lubricating characteristics when the tubular main body is put in and taken out with respect to a living body. In addition, since non-lubricating characteristics are exhibited when the temperature of the temperature responsive lubricating coating layer reaches a temperature equal to or higher than the critical temperature, it is possible to retain the tubular main body on the proximal side and to prevent an imprudent (i.e., unintended) movement from occurring in the tubular main body.

DETAILED DESCRIPTION

Set forth below with reference to the accompanying drawings is a detailed description of embodiments of an elongated medical body representing examples of the inventive elongated medical body disclosed here.

Figure 1:
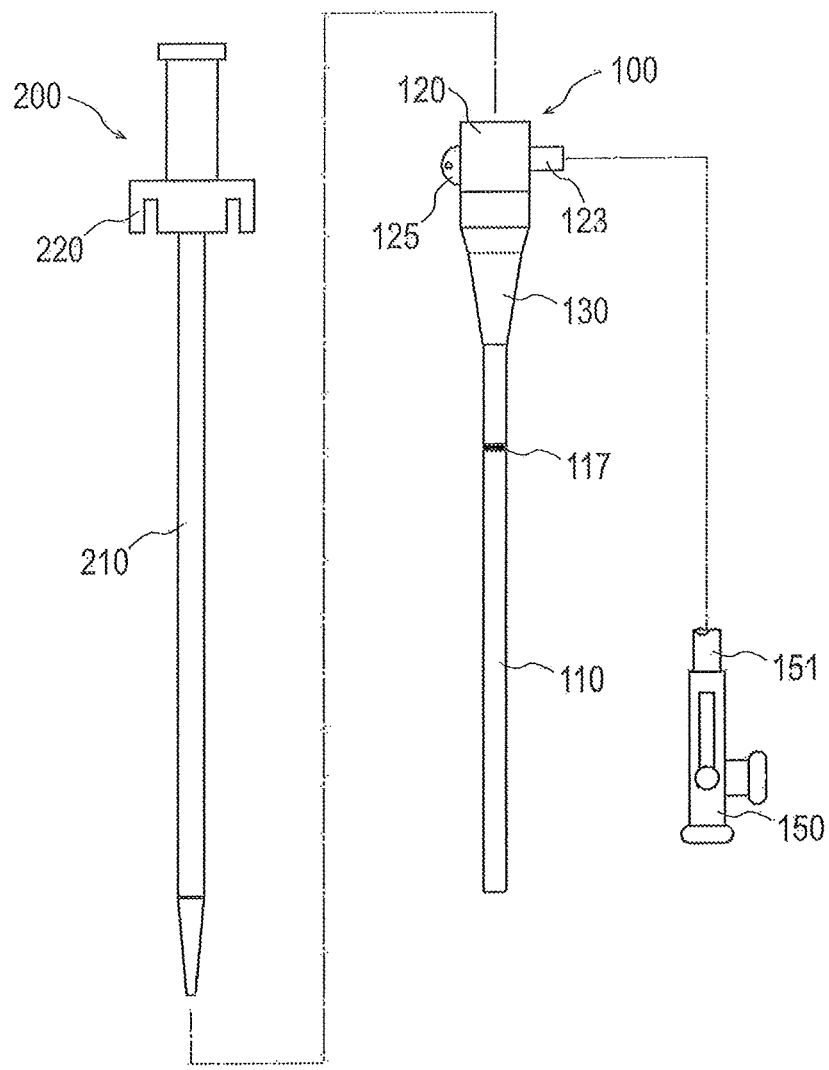
FIG. 1 is a view illustrating an introducer according to an embodiment.
Figure 2:
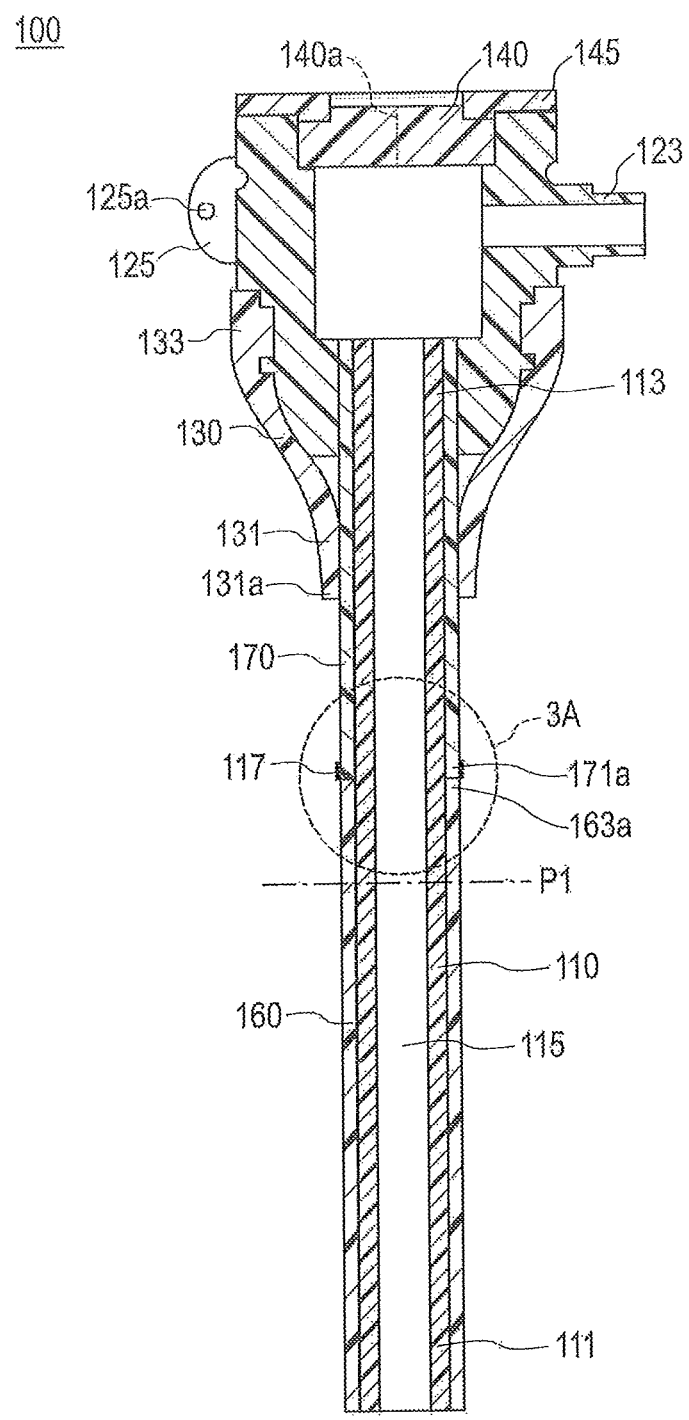
FIG. 2 is a sectional view of an introducer sheath of the embodiment shown in FIG. 1.
Figure 3:
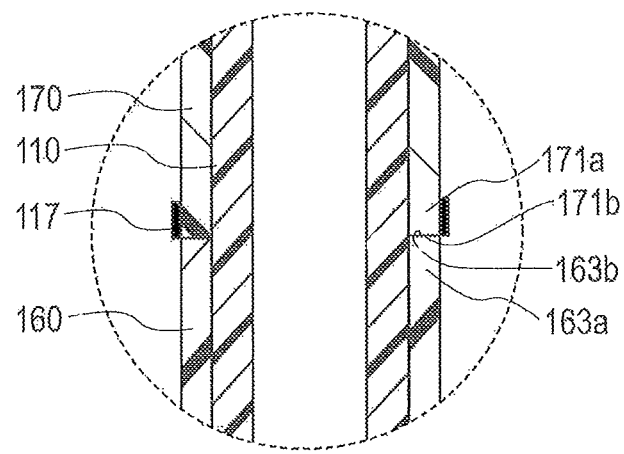
FIG. 3 is an enlarged view illustrating a dotted line area 3A of FIG. 2.
Figure 4:
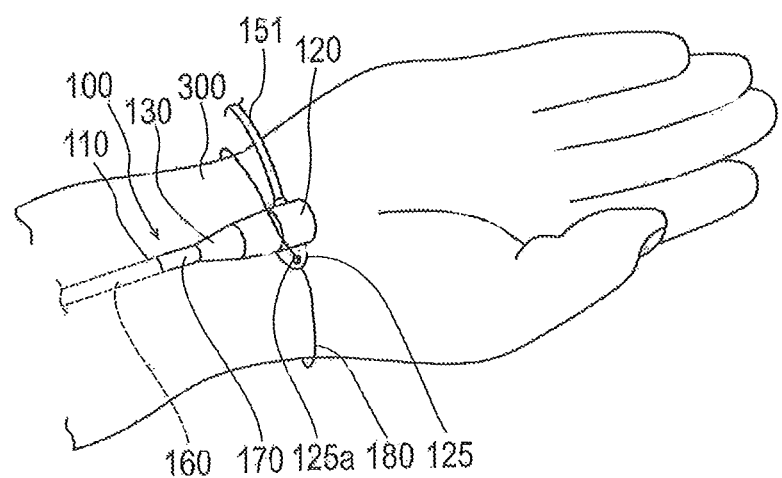
FIG. 4 is a perspective view illustrating a usage state of the introducer sheath of the embodiment shown in FIG. 1.

An embodiment of a medical elongated body 100 will first be described with reference to FIGS. 1 to 4. In this specification, an embodiment in which the medical elongated body 100 is applied to an introducer sheath will be described. FIG. 1 illustrates an introducer 10 including an introducer sheath 100. FIGS. 2 and 3 illustrate sectional views along an axial direction of the introducer sheath 100. FIG. 4 illustrates a usage state of the introducer sheath 100.

In this specification, the side of the introducer sheath 100 on which a sheath hub 120 is disposed will be referred to as a proximal side or proximal end. In addition, the side of the introducer sheath 100 positioned opposite to the proximal side and which is introduced into a living body will be referred to as a distal side or distal end. The direction in which the introducer sheath 100 extends will be referred to as the axial direction. A "distal portion" denotes a certain range including a distal end (outermost distal end) and surroundings thereof (i.e., the portion adjacent to the distal end), and a proximal portion denotes a certain range including a proximal end (innermost proximal end) and surroundings thereof (i.e., the portion adjacent to the proximal end).

The introducer 10 according to the embodiment illustrated in FIG. 1 has the introducer sheath 100 and a dilator 200.

The introducer sheath 100 indwells inside a blood vessel. For example, elongated bodies such as a catheter and a guide wire are inserted through the inside of the introducer sheath 100, which is then used for introducing the elongated bodies into the blood vessel.

As illustrated in FIG. 2, the introducer sheath 100 has a sheath tube (corresponding to a tubular main body) 110 that includes a hollow portion 115 (i.e., a lumen) extending in the axial direction from a distal portion 111 to a proximal portion 113. The proximal end of the sheath tube 110 is connected to the sheath hub (corresponding to a hub) 120. A strain relief 130 is supported by (i.e., positioned at or connected to) the distal side of the sheath hub 120. The strain relief 130 surrounds a predetermined range of the sheath tube 110 on the proximal side (i.e., the strain relief 130 axially overlaps and circumferentially surrounds a predetermined proximal portion of the sheath tube 110 as shown in FIG. 2).

The sheath tube 110 is configured to be percutaneously introduced into a blood vessel (e.g., as shown in FIG. 4). As described below, a hydrophilic lubricating coating layer 160 and a temperature responsive lubricating coating layer 170 are formed on an outer surface of the sheath tube 110.

The sheath tube 110 material, for example, can be a polymer material such as polyolefin (for example, polyethylene, polypropylene, polybutene, an ethylene-propylene copolymer, an ethylene-vinyl acetate copolymer, an ionomer, and a mixture of two or more of these materials), a polyolefin elastomer, a cross-linked body of polyolefin, polyvinyl chloride, polyamide, a polyamide elastomer, polyester, a polyester elastomer, polyurethane, a polyurethane elastomer, a fluorine resin, polycarbonate, polystyrene, polyacetal, polyimide, polyether imide, polyether ether ketone, and a mixture thereof.

A side port 123 for communicating with the inside of the sheath tube 110 is formed in the sheath hub 120 as shown in FIG. 2. For example, one end of a polyvinyl chloride tube 151 having flexibility (e.g., as shown in FIG. 1) is liquid-tightly connected to the side port 123. A three-way stopcock 150, for example, may be mounted in the other end of the tube 151 as shown in FIG. 1. For example, a liquid such as a physiological salt solution (saline) can be injected into the hollow portion 115 of the sheath tube 110 through a port of the three-way stopcock 150 via the tube 151.

The sheath hub 120 material is not particularly limited. It is preferable to employ a hard material such as a hard resin. Specific examples of the hard resin include polyolefin such as polyethylene and polypropylene; polyamide; polycarbonate; and polystyrene.

A hemostasis valve 140 preventing leaking-out (i.e., unintended discharge) of blood which has flowed into the sheath tube 110 is attached to the sheath hub 120. The hemostasis valve 140 is formed of an elastic member. The hemostasis valve 140 includes a slit 140a allowing a dilator main body 210 to be inserted through the slit 140a. The hemostasis valve 140 is formed to have a substantially elliptical membrane shape (disk shape) and is liquid-tightly fixed to the sheath hub 120 due to a predetermined fitted cap 145.

The hemostasis valve 140 material is not particularly limited. Examples of materials that may be used for the hemostasis valve include elastic members such as silicone rubber, latex rubber, butyl rubber, and isoprene rubber.

A suture eye 125 is provided on the sheath hub 120. The suture eye 125 has a hole 125a through which a fixing tool (for example, a string) may be inserted when the sheath hub 120 is fixed to a limb (for example, a wrist) of a living body (refer to FIG. 4). Note that, the sheath hub 120 does not have to have the suture eye 125.

The strain relief 130 is externally fitted to the sheath tube 110 and the sheath hub 120. A distal portion 131 of the strain relief 130 is disposed to surround a certain range of a proximal portion of the sheath tube 110. A proximal portion 133 of the strain relief 130 is disposed to surround a certain range of a distal portion of the sheath hub 120.

The strain relief 130 material is not particularly limited. Examples thereof include natural rubber and a silicone resin.

As illustrated in FIG. 1, the dilator 200 has the dilator main body 210 which is a tubular body that can be inserted through the sheath tube 110 and a dilator hub 220 configured to be able to be connected (i.e., connectable) to the sheath hub 120.

The dilator 200 is used for preventing a fracture of the sheath tube 110 or for increasing the diameter of a puncture hole in skin of a living body (e.g., patient) when the sheath tube 110 of the introducer sheath 100 is inserted into a blood vessel.

When the dilator main body 210 is inserted through the inside of the sheath tube 110, the distal portion of the dilator main body 210 protrudes beyond the distal end of the sheath tube 110 (i.e., the dilator main body 210 protrudes distally beyond the sheath tube 110). The distal portion of the dilator main body 210 is formed to have a tapered shape tapered toward the distal side (i.e., the distal end of the dilator main body 210 is a tapered tip as shown in FIG. 1 that increases in outer diameter in the proximal direction).

The dilator main body 210 material may be, for example, a polymer material such as polyolefin (for example, polyethylene, polypropylene, polybutene, an ethylene-propylene copolymer, an ethylene-vinyl acetate copolymer, an ionomer, and a mixture of two or more of these materials), a polyolefin elastomer, a cross-linked body of polyolefin, polyvinyl chloride, polyamide, a polyamide elastomer, polyester, a polyester elastomer, polyurethane, a polyurethane elastomer, a fluorine resin, polycarbonate, polystyrene, polyacetal, polyimide, polyether imide, and a mixture of two or more of these materials.

The material of the dilator hub 220 is not particularly limited. It is preferable to employ a hard material such as a hard resin. Specific examples of the hard resin include polyolefin such as polyethylene and polypropylene; polyamide; polycarbonate; and polystyrene.

Next, the hydrophilic lubricating coating layer 160 and the temperature responsive lubricating coating layer 170 formed on the outer surface of the sheath tube 110 will be described.

The hydrophilic lubricating coating layer 160 is a coating layer which exhibits lubricating characteristics when wet. The temperature responsive lubricating coating layer 170 is a coating layer which exhibits hydrophilic characteristics and lubricating characteristics (i.e., acts as a lubricant to decrease friction on the outer surface of the sheath tube 110) at a temperature lower than a critical temperature when the temperature responsive lubricating coating layer 170 is wet. The temperature responsive lubricating coating layer 170 exhibits hydrophobic characteristics and non-lubricating characteristics (i.e., acts to increase friction on the outer surface of the sheath tube 110) at a temperature equal to or higher than the critical temperature when the temperature responsive lubricating coating layer 170 is wet. That is, the hydrophilic lubricating coating layer 160 is relatively lubricious in a living body and the temperature responsive lubricating coating layer 170 is initially relatively lubricious in the living body and then become less lubricious (i.e., possesses a lubricity that imparts greater friction than the hydrophilic lubricating coating layer 160 and the temperature responsive lubricating coating layer 170 at the lower temperature) when the temperature of the coating increases to the critical temperature. As illustrated in FIG. 2, the temperature responsive lubricating coating layer 170 is disposed on the proximal side relative to the hydrophilic lubricating coating layer 160 and is formed on the proximal side of the sheath tube 110. That is, the hydrophilic lubricating coating layer 160 is applied to a portion of the sheath tube 110 entirely distal to the portion of the sheath tube 110 that the temperature responsive lubricating coating layer 170 is applied.

The hydrophilic lubricating coating layer 160 (lubricating characteristics imparting material) is a material exhibiting hydrophilic characteristics and swelling characteristics (i.e., the hydrophilic lubricating coating layer 160 expands (increases in volume) by absorbing the aqueous solvent) when in contact with an aqueous solvent. A layer including such a material is smoothly inserted due to hydrophilic characteristics and lubricating characteristics (surface lubricating characteristics) of the hydrophilic lubricating coating layer 160 when the sheath tube 110 is inserted into a body, so that operability of an operator can be improved (i.e., the movable within a living body with relatively low friction). In addition, when the sheath tube 110 is inserted into a blood vessel, for example, damage to tissue is reduced due to hydrophilic characteristics and lubricating characteristics (surface lubricating characteristics) of the sheath tube 110, so that a burden to a patient can be reduced.

The lubricating characteristics imparting material used for the hydrophilic lubricating coating layer 160 is not particularly limited. Any material can be used as long as the material exhibits hydrophilic characteristics and swelling characteristics when in contact with the aqueous solvent. Examples of materials that may be used include a copolymer of an epoxy group-containing monomer such as glycidyl acrylate, glycidyl methacrylate, 3,4-epoxy cyclohexyl methyl acrylate, 3,4-epoxy cyclohexyl methyl methacrylate, β-methyl glycidyl methacrylate, and allyl glycidyl ether, and a hydrophilic monomer such as N-methyl acrylamide, N,N-dimethylacrylamide, and acrylamide; a polymer (copolymer) formed of the aforementioned hydrophilic monomer; a cellulosic polymer substance such as hydroxypropyl cellulose, and carboxymethyl cellulose; and polysaccharide, polyvinyl alcohol, a methyl vinyl ether-maleic anhydride copolymer, water-soluble polyamide, poly (2-hydroxyethyl (meth) acrylate), polyethylene glycol, polyacrylamide, polyvinyl pyrrolidone, and a copolymer of polyvinyl pyrrolidone and polyurethane disclosed in U.S. Pat. No. 4,100,309 and Japanese Patent Application Publication No. 59-19582. The lubricating characteristics imparting material may be used alone with one kind or may be used in a form of a mixture of two or more kinds.

The method of forming the hydrophilic lubricating coating layer 160 is also not particularly limited. A known method can be applied in a similar manner or in a suitably modified manner. For example, it is preferable that a coating liquid is prepared by adding the lubricating characteristics imparting material to an appropriate solvent. A predetermined portion of the outer surface of the sheath tube 110 is then coated with the coating liquid. The method of coating the outer surface of the sheath tube 110 is not particularly limited. It is possible to use, for example, a coating/printing method, an immersing method (dipping method and dip-coating method), an atomizing method (spraying method), bar coating, die coating, spin coating, gravure coating, and a mixed solution-impregnated sponge coating method.

The solvent is not particularly limited as long as the lubricating characteristics imparting material can be dissolved. The solvent can be suitably selected in accordance with the type of the lubricating characteristics imparting material to be used. Specifically, examples of solvents that may be used include water; alcohols such as methanol, ethanol, isopropanol, and ethylene glycol; ketones such as acetone, methyl ethyl ketone, and cyclohexanone; esters such as ethyl acetate; halides such as chloroform; olefins such as hexane; ethers such as tetrahydrofuran and butyl ether, aromatic compounds such as benzene and toluene; amides such as N,N-dimethylformamide (DMF); sulfoxides such as dimethylsulfoxide. The solvent is not limited, however, to only these materials. The solvent(s) may be used alone with one kind, or two or more kinds of solvents may be used together.

The concentration of the lubricating characteristics imparting material of the coating liquid is not particularly limited. From a viewpoint of coating characteristics, a desired effect (hydrophilic characteristics and lubricating characteristics imparting effect), and the like, the concentration of the lubricating characteristics imparting material of the coating liquid ranges from 0.01 to 20 weight %. The concentration of the lubricating characteristics imparting material of the coating liquid more preferably may range from 0.05 to 15 weight % and ranges still more preferably from 0.1 to 10 weight %. If the concentration of the lubricating characteristics imparting material is within the ranges above, an acquired hydrophilic lubricating coating layer has (relatively) excellent hydrophilic characteristics or lubricating characteristics. In addition, using a concentration within the range(s) discussed above is preferable in regard to operability (for example, easiness of coating) and production efficiency because a uniform hydrophilic lubricating coating layer 160 having a desired thickness can be rather easily acquired with one coating. Even if the concentration of the lubricating characteristics imparting material, however, is beyond the above-described ranges, the concentration can be acceptably used as long as the concentration is within a range which does not affect the operational effect of the sheath tube. In addition, the above-described coating step may be repetitively performed in accordance with desired hydrophilic characteristics and lubricating characteristics.

A material forming the temperature responsive lubricating coating layer 170 (temperature responsive material) is a material that exhibits hydrophilic characteristics and lubricating characteristics at a temperature lower than a predetermined critical temperature (for example, near a body temperature) and on the other hand, exhibits hydrophobic characteristics and resistant characteristics (non-lubricating characteristics that increase friction or reduce the lubricious qualities when moved within the living body) at a temperature equal to or higher than the predetermined critical temperature. Similar to the hydrophilic lubricating coating layer 160, the temperature responsive lubricating coating layer 170 includes such a material so that the sheath tube 110 can be smoothly inserted and moved within the living body due to hydrophilic characteristics and lubricating characteristics (surface lubricating characteristics), so that operability of an operator can be improved. In addition, for example, when the sheath tube 110 is inserted into a blood vessel, damage to body tissue is reduced due to the hydrophilic characteristics and lubricating characteristics (surface lubricating characteristics) of the temperature responsive lubricating coating layer 170, so that a burden to a patient can be reduced. After the sheath tube 110 indwells in a body, the sheath tube 110 is warmed (increases in heat) to a temperature near the body temperature, so that the layer exhibits hydrophobic characteristics and resistant characteristics (non-lubricating characteristics). Therefore, due to frictional resistance between the sheath tube 110 and an insertion site, the sheath tube 110 can be easily retained at a predetermined position on a body surface. The temperature responsive material is not particularly limited and any material can be used as long as the above-described characteristics are exhibited. Lubricating characteristics are exhibited at a temperature lower than the body temperature and are preferably exhibited at room temperature. It is preferable that non-lubricating characteristics (i.e., friction-increasing characteristics) are exhibited at a temperature lower than the body temperature. The critical temperature ranges from 25° C. to 35° C., and the critical temperature more preferably ranges from 30° C. to 35° C. in order to sufficiently maintain lubricating characteristics at the time of puncturing. Specifically, examples of materials that can be used as the temperature responsive material include an amide-based polymer such as poly-N-isopropyl acrylamide, poly-N-isopropyl methacrylamide, poly-N-ethyl (meth) acrylamide, poly-N-n-propyl (meth) acrylamide, poly-N-cyclopropyl (meth) acrylamide, poly-N,N-ethylmethyl (meth) acrylamide, poly-N,N-diethyl (meth) acrylamide, poly-N-acrylic prolidine, poly-N-acrylic piperidine, poly-N-vinyl pyrrolidone, and poly-ethyl oxazoline; an alcohol-based polymer such as partial oxide of polyvinyl alcohol, polyvinyl methyl ether, a polyvinyl alcohol derivative, methyl cellulose, polyhydroxypropyl acrylate, hydroxypropyl methyl cellulose, and hydroxypropyl cellulose; a polyether-based polymer such as polyethylene oxide, a copolymer of ethylene oxide-propylene oxide, a block copolymer of polyethylene oxide-polypropylene oxide-polyethylene oxide, a block polymer of alkyl-polyethylene oxide, and polymethylvinyl ether; and a carboxylic acid-based polymer such as polymethacrylic acid. The temperature responsive material(s) may be used alone with one kind or may be used in a form of a mixture of two or more kinds of these materials. In addition, it is also possible to preferably utilize a polymer obtained by suitably copolymerizing a hydrophilic monomer or a hydrophobic monomer for the purpose of controlling the critical temperature of the temperature responsive material. If a hydrophilic monomer is copolymerized in the temperature responsive material, the critical temperature rises. If a hydrophobic monomer is copolymerized in the temperature responsive material, the critical temperature falls. Utilizing these properties, it is possible to suitably adjust the critical temperature in accordance with the usage purpose of the device. In addition to the above-described monomer or in place of the above-described monomer, it is also possible to suitably utilize a polymer obtained by copolymerizing a different monomer for the purpose of enhancing membrane strength of the temperature responsive lubricating coating layer 170 or improving bonding characteristics with a substrate. The different monomer is not particularly limited and is suitably selected in accordance with the type and the like of the substrate. Specifically, it is possible to particularly and preferably use an epoxy group-containing monomer such as glycidyl acrylate, glycidyl methacrylate, 3,4-epoxy cyclohexyl methyl acrylate, 3,4-epoxy cyclohexyl methyl methacrylate, β-methyl glycidyl methacrylate, and allyl glycidyl ether.

The method of forming the temperature responsive lubricating coating layer 170 is not particularly limited. A known method can be applied in a similar manner or in a suitably modified manner. For example, it is preferable that a coating liquid is prepared by adding the temperature responsive material to an appropriate solvent. A predetermined position on the outer surface of the sheath tube 110 (i.e., a predetermined portion of the outer surface of the sheath tube 110) is then coated with the coating liquid. The coating method is not particularly limited. Specifically, it is possible to use a coating method similar to that for the solvent described in the example of the method of forming the hydrophilic lubricating coating layer 160. The type of solvent is not particularly limited as long as the temperature responsive material can be dissolved. The solvent can be suitably selected in accordance with the type of the temperature responsive material to be used. Specifically, it is possible to use a solvent similar to the solvent described above in the example of the method of forming the hydrophilic lubricating coating layer 160.

The concentration of the temperature responsive material in the coating liquid is not particularly limited. From a viewpoint of coating characteristics, a desired effect (hydrophilic characteristics and lubricating characteristics imparting effect), and the like, the concentration of the lubricating characteristics imparting material of the coating liquid ranges from 0.01 to 20 weight %, ranges more preferably from 0.05 to 15 weight %, and ranges still more preferably from 0.1 to 10 weight %. If the concentration of the lubricating characteristics imparting material is within the above-described range, an acquired temperature responsive lubricating coating layer 170 exhibits sufficient hydrophilic characteristics and lubricating characteristics at a temperature lower than a predetermined temperature (for example, the temperature of the living body). The acquired temperature responsive lubricating coating layer 170 also exhibits sufficient hydrophobic characteristics and resistant characteristics (non-lubricating characteristics) at a temperature equal to or higher than the predetermined temperature. Since the temperature responsive lubricating coating layer 170 can be uniformly formed at a desired thickness relatively easily in one coating, it is preferable in regard to operability (for example, easiness of coating) and production efficiency. Even if the concentration is beyond the above-described range, however, the concentration used can be acceptable as long as the concentration is within a range which does not affect the operational effect of the sheath tube. In addition, the above-described coating step may be repetitively performed to achieve any particular desired characteristics of the coating.

The proximal end 163a of the hydrophilic lubricating coating layer 160 is disposed on the proximal side of the sheath tube 110 relative to a center position P1 in the axial direction of the sheath tube 110 as shown in FIG. 2 (i.e., the proximal end 163a of the hydrophilic lubricating coating layer 160 is proximal to the center position P1 in the axial direction of the sheath tube 110). That is, the hydrophilic lubricating coating layer 160 is formed over half or more of the overall length of the sheath tube 110. For example, the sheath tube 110 can be formed to have an axial length within a range from 7 mm to 33 mm. In this case, for example, the length of the hydrophilic lubricating coating layer 160 from the distal end of the sheath tube 110 can be formed within a range from 3.5 mm to 29.5 mm.

As illustrated in FIG. 2, the temperature responsive lubricating coating layer 170 is formed on the outer surface of the sheath tube 110 over a predetermined range from the distal side of the sheath tube 110 relative to a distal end 131a of the strain relief 130 (i.e., from distal to the distal end 131a of the strain relief 130) to the proximal side of the sheath tube 110 relative to the distal end 131a of the strain relief 130 (i.e., to proximal to the distal end 131a of the strain relief 130). In this manner, the temperature responsive lubricating coating layer 170 is formed from the distal side to the proximal side of the distal end 131a of the strain relief 130.

At least a part of the temperature responsive lubricating coating layer 170 can be disposed to be in contact with the hydrophilic lubricating coating layer 160 as illustrated in FIG. 3. In the present embodiment, an end surface (proximal end surface) 163b on the proximal end 163a side of the hydrophilic lubricating coating layer 160 and an end surface (distal end surface) 171b on a distal end 171a side of the temperature responsive lubricating coating layer 170 are directly in contact while facing each other. Resistance when the sheath tube 110 is inserted and removed is reduced by preventing a step (i.e., a radial outward protrusion) from being formed in a joining portion between the layers 160 and 170 in this manner.

A marker 117 is formed on the proximal side of the sheath tube 110 as illustrated in FIGS. 2 and 3. For example, the distal end 171a of the temperature responsive lubricating coating layer 170 can axially overlap the marker 117 or be positioned distal to the marker 117. In the example illustrated in FIGS. 2 and 3, the end surface 171b on the distal end 171a side of the temperature responsive lubricating coating layer 170 is disposed at a position overlapping the end surface of the marker 117 on the distal side in the axial direction. The marker 117 can be formed, for example, by applying a different color than a color of the temperature responsive lubricating coating layer 170 in the entire outer circumference of the temperature responsive lubricating coating layer 170 or a portion of the outer circumference of the temperature responsive lubricating coating layer 170.

It is preferable that the marker 117 is formed in a predetermined region of the sheath tube 110 on the proximal side before the sheath tube 110 is coated with the hydrophilic lubricating coating layer 160 or coated with the temperature responsive lubricating coating layer 170. The marker 117 may be formed by applying a color different from that of the temperature responsive lubricating coating layer 170 in the entire outer circumference of the sheath tube 110 or a portion of the outer circumference of the sheath tube 110. When the sheath tube 110 is coated with the hydrophilic lubricating coating layer 160 or the temperature responsive lubricating coating layer 170, the hydrophilic lubricating coating layer 160 or the temperature responsive lubricating coating layer 170 can thus be formed based on the marker 117.

For example, the sheath tube 110 and/or the temperature responsive lubricating coating layer 170 may include a coloring matter (e.g., a visible coloring agent) for discriminating (visually determining) the position at which the temperature responsive lubricating coating layer 170 is formed. The coloring matter may be applied/formed by, for example, adding a coloring agent to the sheath tube 110 and/or the temperature responsive lubricating coating layer 170. A pigment can be used, for example, as the coloring agent. For example, an inorganic pigment and an organic pigment known in the related art can be used. Examples of the inorganic pigment include carbon black, titanium oxide, barium sulfate, iron oxide (black iron oxide, yellow iron oxide, red iron oxide), chromium oxide, ultramarine blue (ultramarine-based blue and ultramarine-based violet), nickel titanium yellow, prussian blue, milorie blue, cobalt blue, viridian, and molybdenum red. Examples of the organic pigment include pigments such as a quinacridone-based pigment (for example, quinacridone-based red), a perylene-based pigment (for example, perylene-based red), an anthraquinone-based pigment (for example, anthraquinone-based yellow), an azo-based pigment (for example, a condensed azo-based yellow organic pigment), and a phthalocyanine-based pigment (for example, halogenated phthalocyanine such as copper phthalocyanine and high copper chloride phthalocyanine). It is possible to suitably employ a color such as black, red, green, blue, yellow, purple, and white as the color of the coloring matter (coloring agent).

For example, the coloring matter included in the sheath tube 110 and/or the temperature responsive lubricating coating layer 170 may change in color in response to a temperature change. It is thus possible to easily check whether the temperature responsive lubricating coating layer 170 is in a wet state or a non-wet state based on the color.

Next, a usage example and an operation of the sheath tube 110 according to the present embodiment will be described.

FIG. 4 illustrates a situation in which the distal side of the sheath tube 110 is inserted into a blood vessel and the proximal side is disposed outside a living body. In this state, the distal side of the sheath tube 110 (on which the hydrophilic lubricating coating layer 160 is formed) manifests favorable lubricating characteristics by being in contact with blood or the like. Meanwhile, the proximal side of the sheath tube 110 (on which the temperature responsive lubricating coating layer 170 is formed) is warmed by coming into contact with an outer layer of a living body. If the temperature responsive lubricating coating layer 170 warms to reach a temperature equal to or higher than the critical temperature, non-lubricating characteristics are manifested.

In this usage example, the sheath tube 110 is inserted into a radial artery traveling along a wrist 300. In a blood vessel such as a radial artery, there are cases where the volume of blood flow on a peripheral side (side distant from the heart) temporarily increases and a pressure in a direction removing from a puncture site acts on the sheath tube 110 due to constriction (twitch) and relaxation of the blood vessel. Even when such a pressure acts, the proximal side of the sheath tube 110 is retained on an outer layer of a living body in a positionally fixed manner because the temperature responsive lubricating coating layer 170 is formed in the sheath tube 110. Therefore, it is possible to help prevent misalignment of the sheath tube 110 within the living body or unintended withdrawal of the sheath tube 110 from the living body.

During treatment using the introducer sheath 100, there may be cases where the introducer sheath 100 is fixed to the wrist 300 by utilizing a fixing string 180 passing through the hole 125a of the suture eye 125 as shown in FIG. 4. For example, when the hydrophilic lubricating coating layer 160 is formed on the proximal side of the sheath tube 110, there are cases where the strain relief 130 slides with respect to the sheath tube 110 and the strain relief 130 rotates if lubricating characteristics of the hydrophilic lubricating coating layer 160 continue during treatment using the introducer sheath 100. If rotation of the strain relief 130 occurs, the sheath hub 120 connected to the strain relief 130 also rotates. As a result, it may be difficult for an operator to check for various indications (for example, indication of size of the sheath tube 110) stated in the strain relief 130. The fixing string 180 may also move due to rotation of the suture eye 125, so that it may be difficult to realize a smooth technique. In regard to these operational difficulties, the temperature responsive lubricating coating layer 170 is formed in the distal end 131a of the strain relief 130 and over the distal side and the proximal side of the distal end 131a of the strain relief 130 as well, so that the temperature of the temperature responsive lubricating coating layer 170 during treatment reaches a temperature equal to or higher than the critical temperature. Consequently, frictional resistance between the sheath tube 110 and the strain relief 130 increases, so that it is possible to help prevent unintended rotation of the strain relief 130.

When the sheath tube 110 is inserted into a blood vessel, it is preferable that the sheath tube 110 is wetted with a liquid such as saline having a temperature lower than the body temperature of a patient. Wetting the sheath tube 110 with saline causes the hydrophilic lubricating coating layer 160 and the temperature responsive lubricating coating layer 170 to exhibit lubricating characteristics (i.e., be relatively lubricious). Meanwhile, after the sheath tube 110 is inserted into a blood vessel, a part of the sheath tube 110 in which the temperature responsive lubricating coating layer 170 is formed may be aggressively warmed to a temperature equal to or higher than the critical temperature such that the temperature responsive lubricating coating layer 170 exhibits non-lubricating characteristics (i.e., become relatively non-lubricious or increase in frictional resistance). For example, the part of the sheath tube 110 may reach a temperature equal to or higher than the critical temperature by utilizing heat transferred from an outer layer of a living body. In addition, when the sheath tube 110 is removed from a blood vessel, the temperature responsive lubricating coating layer 170 may be cooled with a liquid such as saline having a temperature lower than the body temperature of a patient such that the temperature responsive lubricating coating layer 170 reaches a temperature equal to or lower than the critical temperature. Consequently, the sheath tube 110 can be easily removed from a living body.

In the introducer sheath 100 described above, it is possible to smoothly move the sheath tube 110 in a low-invasive manner because each of the hydrophilic lubricating coating layer 160 and the temperature responsive lubricating coating layer 170 exhibits lubricating characteristics when the sheath tube 110 is put in and taken out with respect to a living body. In addition, since non-lubricating characteristics are exhibited when the temperature of the temperature responsive lubricating coating layer 170 reaches a temperature equal to or higher than the critical temperature, it is possible to retain the sheath tube 110 on the proximal side and to prevent an imprudent (unintended) movement from occurring in the sheath tube 110.

Since the hydrophilic lubricating coating layer 160 is formed over half or more of the overall length of the sheath tube 110, a certain region of the distal side of the sheath tube 110 can have lubricating characteristics by being wet. Since the temperature responsive lubricating coating layer 170 is formed, it is possible to prevent invasiveness at the time of insertion from increasing.

The temperature responsive lubricating coating layer 170 is formed on the outer surface of the sheath tube 110 over a predetermined range from the distal side relative to the distal end 131a of the strain relief 130 to the proximal side relative to the distal end 131a. Therefore, it is possible to preferably prevent the strain relief 130 from rotating with respect to the sheath tube 110.

The temperature of the temperature responsive lubricating coating layer 170 can be raised to a temperature equal to or higher than the critical temperature by the body temperature of a living body because the critical temperature of the temperature responsive lubricating coating layer 170 is 35° C. or lower. This critical temperature allows the non-lubricating characteristics to be manifested without separately performing work such as warming.

Lubricating characteristics can be successively manifested from the distal side to the proximal side of the sheath tube 110 because at least a part of the temperature responsive lubricating coating layer 170 is in contact with the hydrophilic lubricating coating layer 160. Therefore, it is possible to prevent insertion resistance from occurring in a border part between the two layers 160 and 170.

A marker 117 can be formed on the proximal side of the sheath tube 110. The distal end 171a of the temperature responsive lubricating coating layer 170 is disposed at a position overlapping the marker 117 or at a position on the distal side relative to the marker 117. Accordingly, when the sheath tube 110 is inserted into a blood vessel, the border part between the hydrophilic lubricating coating layer 160 and the temperature responsive lubricating coating layer 170 can be easily and visually checked by the operator. If the sheath tube 110 is inserted into a living body at least to a part in which the marker 117 is formed, the part in which the temperature responsive lubricating coating layer 170 of the sheath tube 110 is formed can be reliably disposed outside the living body. Accordingly, it is possible to preferably prevent movement or accidental removal of the sheath tube 110 occurring due to the hydrophilic lubricating coating layer 160 disposed on an outer layer of a living body.

The sheath tube 110 and/or the temperature responsive lubricating coating layer 170 may include the coloring matter (e.g., a coloring agent) for visually determining the position at which the temperature responsive lubricating coating layer 170 is formed. Accordingly, it is possible for the operator to more reliably and easily check for the position at which the temperature responsive lubricating coating layer 170 is formed.

Figure 5:
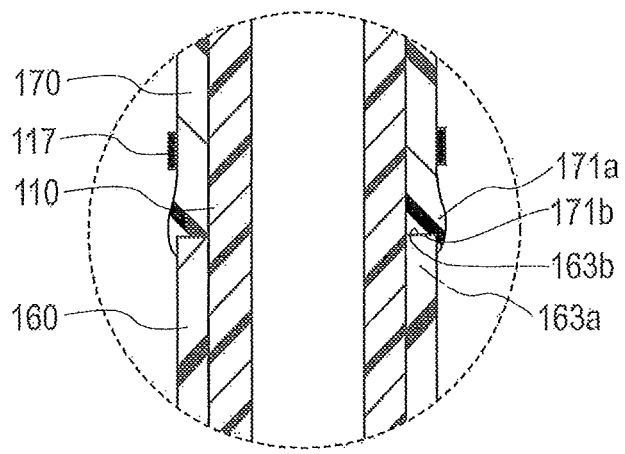
FIG. 5 is an enlarged sectional view illustrating a part of an introducer sheath of another embodiment.

In the exemplary embodiment described above, the end surface 163b on the proximal end 163a side of the hydrophilic lubricating coating layer 160 and the end surface 171b on the distal end 171a side of the temperature responsive lubricating coating layer 170 are disposed while facing each other and the joining portion between the layers 160 and 170 is smoothly formed (e.g., as shown in FIG. 3). However, the disposition relationship between the layers 160 and 170 is not limited to being joined in this manner. For example, FIG. 5 illustrates Modification Example 1 in which the temperature responsive lubricating coating layer 170 is disposed to at least partially cover the hydrophilic lubricating coating layer 160 (i.e., a portion of the distal end of the temperature responsive lubricating coating layer 170 is directly applied to the outer surface of a portion of the proximal end of the hydrophilic lubricating coating layer 160 to axially overlap and cover the hydrophilic lubricating coating layer 160). In this modification example, the proximal end surface 163b of the hydrophilic lubricating coating layer 160 is covered with the distal end 171a of the temperature responsive lubricating coating layer 170. The marker 117 may be disposed on the proximal side of the sheath tube 110 relative to the distal end 171a of the temperature responsive lubricating coating layer 170 as shown in FIG. 5.

Figure 6:
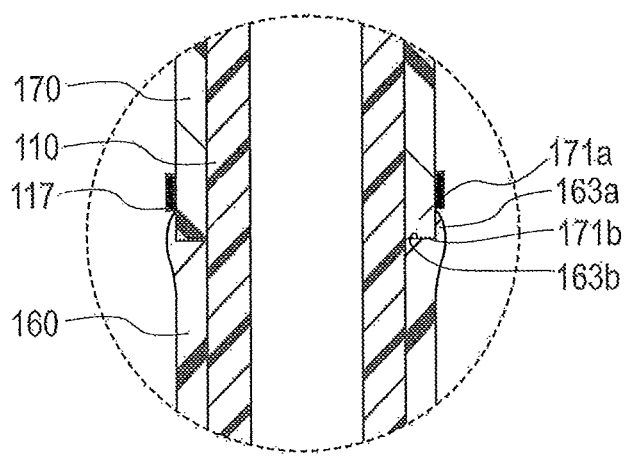
FIG. 6 is an enlarged sectional view illustrating a part of an introducer sheath of another embodiment.

In addition, for example, FIG. 6 illustrates Modification Example 2 where the hydrophilic lubricating coating layer 160 is disposed to at least partially cover the temperature responsive lubricating coating layer 170 (i.e., a portion of the proximal end of the hydrophilic lubricating coating layer 160 is directly applied to the outer surface of a portion of the distal end of the temperature responsive lubricating coating layer 170 to axially overlap and cover the temperature responsive lubricating coating layer 170). In this modification example, the end surface 171b on the distal end 171a side of the temperature responsive lubricating coating layer 170 is covered with the proximal end 163a of the hydrophilic lubricating coating layer 160. The marker 117 may be disposed on the proximal side of the sheath tube 110 relative to the distal end 171a of the temperature responsive lubricating coating layer 170 as shown in FIG. 6.

As illustrated in Modification Examples 1 and 2 of FIGS. 5 and 6, respectively, a manufacturing step is facilitated (i.e., made easier) when the hydrophilic lubricating coating layer 160 and the temperature responsive lubricating coating layer 170 are formed because there is no need to strictly align the position of the joining portion which becomes the border part between the layers 160 and 170 at the time of manufacturing.

An effect of the medical elongated body will be described using examples and comparative examples. However, the technical scope of the medical elongated body is not limited to only the examples below. In the examples, unless otherwise stated, operations were performed at room temperature (25° C.). In addition, unless otherwise stated, "%" and "part" respectively denote "weight %" and "parts by weight".

Moderation Example 1: Synthesis of Temperature Responsive Material (Temperature Responsive Polymer) and Preparation of Coating Liquid After triethylene glycol of 29.7 g was dropped into adipic acid dichloride of 72.3 g at 50° C., hydrochloric acid was removed by depressurizing at 50° C. for three hours. Then, oligoester was acquired. Subsequently, methyl ethyl ketone of 4.5 g was added to the acquired oligoester of 22.5 g, and the mixture was dropped into a solution consisting of sodium hydroxide of 5 g, 31% hydrogen peroxide of 6.93 g, dioctyl phosphate of 0.44 g as a surfactant, and water of 120 g to be subjected to reaction at −5° C. for 20 minutes. The acquired product was dried after being repetitively subjected to water cleaning and methanol washing. Polyperoxide (PPO) having a plurality of peroxide groups in molecules was then acquired. Subsequently, the PPO of 0.5 g as a polymerization initiator, and glycidyl methacrylate (GMA) of 9.5 g were stirred to be polymerized at 65° C. for two hours under a depressurized condition while having benzene as a solvent. A reactant was precipitated again due to diethylether, and poly-GMA (PPO-GMA) having peroxide groups in molecules was acquired.

The acquired PPO-GMA of 0.89 g serving as a polymerization initiator was next dissolved in chlorobenzene together with N-isopropylacrylamide (NIPAAm) of 14.0 g that is a temperature responsive monomer to be polymerized by being heated at 75° C. for eight hours under a nitrogen atmosphere. The reactant was precipitated again due to hexane and was collected. Then, Block Copolymer 1 having an NIPAAm site as a temperature responsive site, and a GMA site as a hydrophobic site having reactive functional groups was produced. The ratio of NIPAAm:GMA of the produced Block Copolymer 1 (that is, the molar ratio of the temperature responsive site and the hydrophobic site in the block copolymer) was 20:1 (molar ratio), and the critical temperature (LCST) of the temperature responsive site was 32° C.

The produced Block Copolymer 1 was dissolved in tetrahydrofuran to achieve concentration of 5 wt %, and a temperature responsive polymer coating liquid was acquired.

Preparation Example 2: Synthesis of Lubricating Characteristics Imparting Agent Quantity (Hydrophilic (Non-temperature Responsive) Polymer) and Preparation of Coating Liquid Similar to Preparation Example 1, poly-GMA (PPO-GMA) was synthesized. Subsequently, the acquired PPO-GMA of 1.43 g serving as a polymerization initiator was dissolved in chlorobenzene together with N,N-dimethylacrylamide (DMAAm) of 20.0 g that is a hydrophilic characteristics monomer to be polymerized by being heated at 75° C. for eight hours under a nitrogen atmosphere. The reactant was precipitated again due to hexane and was collected. Then, Block Copolymer 2 having a DMAAm site as a hydrophilic site, and a GMA site as a hydrophobic site having reactive functional groups was produced. The ratio of DMAAm:GMA of the produced Block Copolymer 2 (that is, the molar ratio of the hydrophilic site and the hydrophobic site in the block copolymer) was 20:1 (molar ratio).

The produced Block Copolymer 2 was dissolved in dimethylformamide to achieve concentration of 5 wt %, and a hydrophilic polymer coating liquid was acquired.

Example 1, Comparative Examples 1 and 2: Coating Sheath (Sheath Tube)

Ethylene tetrafluoro ethylene (ETFE) sheath (5Fr) having a length of 130 mm was prepared, and the prepared sheath was subjected to plasma treatment under an atmospheric pressure. Then, the length of 100 mm on the distal side was subjected to dip coating in the hydrophilic polymer coating liquid acquired in Preparation Example 2. A length of 30 mm on a rear end (proximal end) side was then subjected to dip coating in the temperature responsive polymer coating liquid acquired in Preparation Example 1. The entirety of the sheath was heated at 150° C. for two hours, and the sheath coated with a temperature responsive polymer over 30 mm in the rear end was acquired. Moreover, a printing body colored blue at a temperature lower than 30° C. and colored red at a temperature of 30° C. or higher (manufactured by PILOT INK CO., LTD., Metamo Label) was attached to the most rear end site of the sheath (proximal end) as a temperature indicator, so that the temperature state could be visually distinguished (Example 1).

Ethylene tetrafluoro ethylene (ETFE) sheath (5Fr) having a length of 130 mm was subjected to dip coating throughout the overall length in the hydrophilic polymer coating liquid acquired in Preparation Example 2. The sheath was heated at 150° C. for two hours, and the sheath coated with a hydrophilic polymer throughout the overall length was acquired (Comparative Example 1).

In addition, an uncoated sheath was taken as Comparative Example 2.

<Evaluation>
1. Insertion Characteristics

Each of the sheaths produced in Example 1 and Comparative Examples 1 and 2 was immersed in saline at room temperature (25° C.). Thereafter, a silicone artery model installed in a thermostatic bath at 37° C. was quickly punctured, and the sheath was inserted to a part near the most rear end portion and indwelled in the silicone artery model installed in the thermostatic bath. The temperature indicator of the sheath of Example 1 was colored blue during this time, and the sheath could be inserted into the model without recognizing any significant resistance. Similarly, the sheath of Comparative Example 1 coated with a hydrophilic polymer throughout the overall length could be inserted into the model without any resistance. The uncoated sheath of Comparative Example 2 had significant resistance when inserted into the model and it was difficult for the sheath to be inserted.

2. Indwelling Characteristics

In order to evaluate easiness of falling-out (i.e., unintended removal) of the sheath indwelling in the artery model, the distal-most end of the sheath indwelling in the silicone artery model (which was installed in the thermostatic bath at 37° C.) was connected to a push-pull gauge. The resistance value when the sheath was pulled out at a speed of 5 mm/sec was thus measured. The temperature indicator of the sheath of Example 1 was colored red after the sheath indwelled in the model, and it could be checked that the temperature became equal to or higher than the critical temperature (LCST) of the temperature responsive polymer. The pull-out resistance (removal resistance) of the sheath of Example 1 in this state was 203.3 gf (i.e., a resistance value at which the sheath does not easily fall out). Meanwhile, Comparative Example 1 coated with a hydrophilic polymer throughout the overall length indicated pull-out resistance of 21.7 gf. This pull-out resistance value indicates a possibility that the sheath would fall out unintentionally (i.e., be removed unintentionally) by a slight force.

The pull-out resistance of the uncoated sheath of Comparative Example 2 was 205.0 gf (i.e., a resistance value at which the sheath does not easily become removed).

3. Removal Characteristics

A gauze including saline at 25° C. was pressed near the indwelling portion of the sheath of Example 1 indwelling in the artery model, and the temperature was lowered until the temperature indicator of the sheath of Example 1 was colored blue. The most distal end of the indwelling sheath was connected to a push-pull gauge, and the resistance value when the sheath was pulled out at a speed of 5 mm/sec was measured. The sheath of Example 1 indicated pull-out resistance of 22.3 gf, and it was found that the sheath could be removed with small pull-out resistance similar to that of the sheath coated with a hydrophilic polymer by intentionally lowering the temperature.

The results are summarized in Table 1 below.

TABLE 1

|  | Insertion Characteristics | Indwelling Characteristics | Removal Characteristics |
| --- | --- | --- | --- |
| Comparative Example 1 | ○ | X | ○ |
| Comparative Example 2 | X | ○ | X |
| Example 1 | ○ | ○ | ○ |

The following is supplementary description for Table 1. The sheath of Comparative Example 1 has excellent insertion characteristics and removal characteristics. However, there is a possibility that the sheath will unintentionally fall out (i.e., be removed) while the sheath indwells in the artery model (or an imprudent movement such as rotation will occur). In addition, although the sheath of Comparative Example 2 can be prevented from unintentionally falling out while the sheath indwells in the artery model, insertion characteristics and removal characteristics are deteriorated (i.e., relatively less favorable). The sheath of Example 1 has excellent insertion characteristics and removal characteristics and can be prevented from unintentionally coming out while the sheath indwells in the artery model. More specifically, in the sheath of Example 1, insertion characteristics and removal characteristics are improved due to the temperature of the sheath lowered to a predetermined temperature at the time of insertion and at the time of removal, and the sheath is unlikely to fall out (i.e., accidentally be removed) from the artery model due to the temperature of the sheath being raised to a temperature near the body temperature (temperature equal to or higher than the critical temperature of the temperature responsive polymer) while the sheath indwells in the artery model.

The disclosed medical elongated body has been described in relation to particular embodiments, modification examples, and additional examples. The inventive medical elongated body is not limited to only the configurations described above and can be suitably changed.

For example, the medical elongated body has been described above in an example relating to an introducer sheath. However, an application subject for the medical elongated body need only be a medical device which has a tubular main body configured to be inserted into a living body and is assumed to be used in a state where at least a part of the distal side of the tubular main body is inserted into the living body and in a state where at least a part of the proximal side of the tubular main body is disposed outside the living body. The application subject is not limited to only the introducer sheath.

The configuration of each portion, disposition of the members, and the like described in the embodiment can be suitably changed. In addition, omission of using additional members described in the illustrated drawings and using other additional members can also be suitably performed. As an example, the hydrophilic lubricating coating layer described in the embodiment can be formed on an inner surface of the hollow portion of the tubular main body.

The detailed description above describes a medical elongated body and a method for using the medical elongated body. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical elongated body comprising:
a tubular main body comprising a lumen, the tubular main body extending in an axial direction, the tubular main body possessing an outer surface, a distal portion and a proximal portion;
a hub connected to the proximal portion of the tubular main body, the hub comprising an interior that communicates with the lumen of the tubular main body, the hub possessing a distal portion; and
a strain relief supported by the distal portion of the hub and surrounding a predetermined range of the proximal portion of the tubular main body;
a hydrophilic lubricating coating layer on the outer surface of the tubular main body, the hydrophilic lubricating coating layer exhibiting lubricating characteristics when wet;
a temperature responsive lubricating coating layer on the outer surface of the tubular main body, the temperature responsive lubricating coating layer exhibiting hydrophilic characteristics and lubricating characteristics at a temperature lower than a critical temperature when wet and exhibiting hydrophobic characteristics and non-lubricating characteristics at a temperature equal to or higher than the critical temperature when wet; and
the temperature responsive lubricating coating layer being proximal to the hydrophilic lubricating coating layer on the outer surface of the tubular main body.

2. The medical elongated body according to claim 1, wherein
the tubular main body has an overall length in the axial direction, and
the hydrophilic lubricating coating layer is formed on the outer surface of the tubular main body for at least half of the overall length of the tubular main body.

3. The medical elongated body according to claim 1, wherein
the strain relief possesses a distal end, and
the temperature responsive lubricating coating layer is formed on the outer surface of the tubular main body over a predetermined range from distal relative to the distal end of the strain relief to proximal relative to the distal end of the strain relief, so that the temperature responsive lubricating coating layer both axially overlaps with a portion of the strain relief and extends distally beyond the distal end of the strain relief.

4. The medical elongated body according to claim 1, wherein the critical temperature of the temperature responsive lubricating coating layer is 25° C. to 35° C.

5. The medical elongated body according to claim 1, further comprising:
a marker formed on the proximal portion of the tubular main body, and
the temperature responsive lubricating coating layer possessing a distal end that is at a same position or is distal to the marker in the axial direction.

6. The medical elongated body according to claim 1, wherein at least one of the tubular main body and the temperature responsive lubricating coating layer includes a coloring matter for visually detecting a position of the temperature responsive lubricating coating layer.

7. The medical elongated body according to claim 1, wherein at least a part of the temperature responsive lubricating coating layer is in contact with the hydrophilic lubricating coating layer.

8. The medical elongated body according to claim 7, wherein
the hydrophilic lubricating coating layer possesses an outer surface, and
at least a part of the temperature responsive lubricating coating layer covers the outer surface of the hydrophilic lubricating coating layer.

9. The medical elongated body according to claim 7, wherein
the temperature responsive lubricating coating layer possesses an outer surface, and
at least a part of the hydrophilic lubricating coating layer covers the outer surface of the temperature responsive lubricating coating layer.

10. A medical elongated body comprising:
a tubular main body comprising a lumen extending in an axial direction of the tubular main body and extending throughout the tubular main body, the tubular main body possessing an outer surface, the tubular main body comprising a first portion, a second portion and a third portion in the axial direction, the second portion being immediately adjacent and distal to the first portion, the third portion being immediately adjacent and distal to the second portion;

a hub connected to the first portion of the tubular main body;

a temperature responsive lubricating coating layer which exhibits a first lubricity when wetted by a first fluid whose temperature is lower than a critical temperature and exhibits a second lubricity when wetted by a second liquid whose temperature is equal to or higher than the critical temperature, the temperature responsive lubricating coating layer directly contacting the outer surface of the tubular main body along at least the second portion of the tubular main body;

a hydrophilic lubricating coating layer which possesses a third lubricity when wet, the hydrophilic lubricating coating layer directly contacting the outer surface of the third portion of the tubular main body;

the second lubricity imparting greater frictional resistance than the first lubricity when the tubular main body moves within a living body; and the second lubricity imparting greater frictional resistance than the third lubricity when the tubular main body moves within the living body.

11. The medical elongated body according to claim 10, wherein the temperature responsive lubricating coating layer extends along the outer surface of the tubular main body along the first portion, so that at least a portion of the hub axially overlaps a portion of the temperature responsive lubricating coating layer.

12. The medical elongated body according to claim 10, wherein the temperature responsive lubricating coating layer possess a distal end, the hydrophilic lubricating coating layer possesses a proximal end, and the distal end of the temperature responsive lubricating coating layer directly contacts the proximal end of the hydrophilic lubricating coating layer.

13. The medical elongated body according to claim 10, wherein the tubular main body has an overall length in the axial direction, and the hydrophilic lubricating coating layer is formed on the outer surface of the tubular main body for at least half of the overall length of the tubular main body.

14. The medical elongated body according to claim 10, wherein the temperature responsive lubricating coating layer changes from having the first lubricity to the second lubricity based on a temperature change upon being introduced into the living body.

15. A method comprising:

inserting an elongated tubular body into a living body, the elongated tubular body comprising an outer surface, the elongated tubular body comprising a first portion and a second portion, the second portion being immediately adjacent and proximal to the first portion in an axial direction, the first portion of the elongated tubular body possessing a first frictional resistance, the second portion of the elongated tubular body possessing a second frictional resistance;

increasing the frictional resistance of the second portion of the elongated tubular body when the elongated tubular body is positioned in the living body so that the frictional resistance of the second portion positioned in the living body increases from one frictional resistance to a greater frictional resistance while at the same time not increasing the frictional resistance of the first portion of the elongated tubular body when the elongated tubular body is positioned in the living body; and fixing the second portion of the elongated tubular body at a location in the living body by friction created between the second portion of the elongated tubular body and a portion of the living body, the fixing of the second portion of the elongated tubular body occurring after the increasing of the frictional resistance of the second portion of the elongated tubular body.

16. The method according to claim 15, wherein the outer surface of the first portion of the elongated tubular body is coated with a hydrophilic lubricating coating layer; and the outer surface of the second portion of the elongated tubular body is coated with a temperature responsive lubricating coating layer.

17. The method according to claim 15, further comprising:

applying saline to the first and second portions of the elongated tubular body to wet the first and second portions of the elongated tubular body before inserting the elongated tubular body into the living body.

18. The method according to claim 15, further comprising:

applying saline to the second portion of the elongated tubular body to cool the temperature of the second portion of the elongated tubular body to decrease the second frictional resistance of the second portion of the elongated tubular body before removing the elongated tubular body from the living body.

19. The method according to claim 15, wherein the increasing of the frictional resistance of the second portion of the elongated tubular body comprises contacting both the first and second portions of the elongated tubular body to a fluid that is at a temperature causing an increase in the temperature of the second portion of the elongated tubular body, the increase of the temperature of the second portion of the elongated tubular body increasing the frictional resistance of the second portion of the elongated tubular body.

20. The method according to claim 15, wherein the first portion of the elongated tubular body includes a hydrophilic lubricating coating layer and the second portion of the elongated tubular body includes a temperature responsive lubricating coating layer, the temperature responsive lubricating coating layer being at a first temperature before inserting the elongated tubular body into the living body, and the increasing of the frictional resistance of the second portion of the elongated tubular body comprises contacting both the hydrophilic lubricating coating layer and the temperature responsive lubricating coating layer with a fluid that is at a temperature causing a temperature of the second portion of the elongated tubular body to increase from the first temperature to a temperature higher than the first temperature.

* * * * *